United States Patent
Liang et al.

(10) Patent No.: US 11,998,271 B2
(45) Date of Patent: Jun. 4, 2024

(54) METHODS AND SYSTEMS OF OPTICAL DIAGNOSIS FOR REFRACTIVE EYE EXAMS

(71) Applicants: PERFECT VISION TECHNOLOGY (HK) LTD., Hong Kong (CN); Junzhong Liang, Fremont, CA (US)

(72) Inventors: Junzhong Liang, Fremont, CA (US); Ling Yu, Fremont, CA (US)

(*) Notice: Subject to any disclaimer, the term of this patent is extended or adjusted under 35 U.S.C. 154(b) by 636 days.

(21) Appl. No.: 17/285,449

(22) PCT Filed: Oct. 25, 2018

(86) PCT No.: PCT/US2018/057459
§ 371 (c)(1),
(2) Date: Apr. 14, 2021

(87) PCT Pub. No.: WO2020/086082
PCT Pub. Date: Apr. 30, 2020

(65) Prior Publication Data
US 2021/0338074 A1    Nov. 4, 2021

(51) Int. Cl.
| A61B 3/032 | (2006.01) |
| A61B 3/00 | (2006.01) |
| A61B 3/028 | (2006.01) |
| A61B 3/103 | (2006.01) |

(52) U.S. Cl.
CPC ............ *A61B 3/032* (2013.01); *A61B 3/0058* (2013.01); *A61B 3/0285* (2013.01); *A61B 3/103* (2013.01)

(58) Field of Classification Search
CPC ..... A61B 3/032; A61B 3/0058; A61B 3/0285; A61B 3/103
USPC ....................................................... 351/239
See application file for complete search history.

(56) References Cited

U.S. PATENT DOCUMENTS

| 5,914,772 A | * | 6/1999 | Dyer ..................... A61B 3/028 351/222 |
| 2017/0329154 A1 | * | 11/2017 | Liang .................. A61B 3/0033 |

FOREIGN PATENT DOCUMENTS

| JP | 2013-236902 A | 11/2013 | |
| JP | 2013236902 A | * 11/2013 | ........... A61B 3/0025 |
| WO | 2012-054651 A2 | 4/2012 | |
| WO | WO-2012054651 A2 | * 4/2012 | ............... G02C 7/02 |

(Continued)

OTHER PUBLICATIONS

International Search Report for PCT Application No. PCT/US2018/057459 dated Jul. 23, 2019, 4 pages.

*Primary Examiner* — Mohammed A Hasan
(74) *Attorney, Agent, or Firm* — Klintworth & Rozenblat IP LLP

(57) ABSTRACT

Methods and systems am disclosed in which an optical diagnosis of an eye's optical image quality is performed using a simulated retinal image. An objective measurement of a total wave aberration is obtained, and residual aberrations are computed by subtracting a sphero-cylindrical correction from the total wave aberration. The simulated retinal image is computed by computing a point-spread function from the residual aberrations and convolving the computed point-spread function with an acuity chart. The optical diagnosis includes at least one of: determining excess aberrations, ranking optics of the eye into optical grades, selecting the eye for high-definition eyeglasses, identifying amblyopia or macular diseases, or choosing an objective refraction for vision correction.

26 Claims, 10 Drawing Sheets

(56) References Cited

FOREIGN PATENT DOCUMENTS

WO      2014-085352 A1    6/2014
WO   WO-2014085352 A1 *  6/2014  ........... A61B 3/0025

* cited by examiner

METHODS AND SYSTEMS OF OPTICAL DIAGNOSIS FOR REFRACTIVE EYE EXAMS

RELATED APPLICATIONS

This application is related to International Patent Application No. PCT/US2018/041622, filed on Jul. 11, 2018 and entitled "Methods and Systems of Refraction Automation for Prescribing Eyeglasses; which claims priority to U.S. Provisional Patent Application No. 62/653,700, filed on Apr. 6, 2018 and entitled "Methods and Systems of Refraction Automation for Prescribing Eyeglasses"; all of which are hereby incorporated by reference in full.

BACKGROUND

Conventional refraction processes rely on the experience and skills of an individual eye care professional (e.g., an optometrist or optician) to set the starting and ending points of a spherical power, a cylinder power, and a cylinder axis for an eyeglass prescription.

A block diagram 10 representing a conventional refraction process is shown in FIG. 1. First, an autorefractor 11 is typically used to take an objective measurement of an eye's refractive errors and provide a rough objective prescription in objective refraction step 12, where the objective prescription includes an objective spherical power $F_s$, an objective cylinder power $F_c$ and an objective cylinder angle $F_a$. Second, an eye care professional determines a rough spherical correction in a phoropter 13, and then administrates a subjective optimization of spherical power, cylinder power and cylinder angle based on the objective prescription from step 12. The subjective optimization is based on the experience and skill of the optometrist or optician, and on subjective feedback of the tested subject (i.e., the patient).

Steps 16, 17 and 18 are part of the subjective refraction performed using the phoropter 13. In step 16, the cylinder angle $F_a$ is subjectively optimized by letting the tested subject first see an astigmatism chart and then an acuity chart afterwards. The eye care professional will set and modify the cylinder angle by an amount $F_a$ based on the objective prescription of step 12 as well as feedback of the tested subject. In step 17, the cylinder power $F_c$ is subjectively optimized by having the tested subject view an acuity chart, and an eye care professional will set and modify the cylinder power by an amount $\delta F_c$ based on the objective prescription as well as feedback of the tested subject. In step 18, the spherical power is subjectively optimized by letting the tested subject see an acuity chart, and an eye care professional will set and modify the spherical power $F_s$ by an amount SFs based on feedback of the tested subject. The same process of steps 16, 17 and 18 are repeated for the other eye of the tested subject. In subjective refraction step 14, a final prescription of the eyeglasses is determined for each eye using the subjectively optimized spherical power $F_s+\delta F_s$ of step 18, the subjectively optimized cylinder power $F_c+\delta F_c$ of step 17, and the subjectively optimized cylinder angle $F_a+\delta F_a$ of step 16.

This conventional approach is subjective. It provides a sphero-cylindrical correction, but lacks the capability for optical diagnosis. If a tested eye has poor vision and cannot see 20/20 as the best corrected visual acuity, there is no way to know whether the visual deficiency is due to poor optics or due to poor retinal performance. If a tested eye can see 20/20, which is defined as normal vision, but has poor clarity or sees multiple images, there is no optical diagnosis for the root causes for poor quality of vision even if the acuity is considered normal.

Consequently, although many configurations and methods for vision correction are known in the art, these conventional methods and systems suffer from one or more disadvantages.

SUMMARY

In some embodiments, a method of optical diagnosis of optical image quality for eye exams includes obtaining an objective measurement of a total wave aberration of an eye of a patient using an objective aberrometer module, where the objective measurement includes a sphero-cylindrical correction and residual aberrations. The sphero-cylindrical correction includes an objective spherical power (SPH_o), an objective cylinder power (CYL_o), and an objective cylinder axis (AXIS_o). The residual aberrations is computed by subtracting the sphero-cylindrical correction from the total wave aberration. The sphero-cylindrical correction is obtained through objective vision optimization to achieve a best image quality for the eye. The method also includes computing and displaying a simulated retinal image by calculating a point-spread function from the residual aberrations and convolving the calculated point-spread function with an acuity chart. An optical diagnosis of the eye's optical image quality is performed based on the simulated retinal image, where the optical diagnosis includes at least one of: a) determining excess aberrations in the eye, the excess aberrations being defined as a portion of the residual aberrations that are more than high-order aberrations for normal optics for seeing at least 20/20 with clear vision or for exceptional optics for seeing at least 20/12; b) ranking an optics of the eye into a plurality of optical grades based on the simulated retinal image; c) selecting the eye for which high-definition eyeglasses is delivered if the eye has exceptional optical quality for potentially achieving 20/12 acuity according to the simulated retinal image, wherein the high-definition eyeglasses are made with free-form technology with an incremental step finer than 0.25D for at least a cylinder power CYL; d) identifying amblyopia or macular diseases based on the simulated retinal image and a best corrected visual acuity for the eye, wherein the best corrected visual acuity is subjectively determined; or e) choosing an objective refraction for vision correction, the choosing comprising generating a plurality of objective spherocylindrical corrections that differ from each other in cylinder power, displaying and calculating a plurality of calculated retinal images that correspond to the generated objective sphero-cylindrical corrections, and reviewing the displayed plurality of calculated retinal images.

In some embodiments, a system for optical diagnosis for eye exams includes an objective aberrometer module, an objective refraction software module, and an optical diagnosis module. The objective aberrometer module is configured to obtain an objective measurement of a total wave aberration of an eye of a patient, where the objective measurement does not involve responses from the patient. The objective refraction software module determines, from the total wave aberration of the eye, a sphero-cylindrical correction that includes an objective spherical power (SPH_o), an objective cylinder power (CYL_o), an objective cylinder axis (AXIS_o). The sphero-cylindrical correction achieves a best image quality for the eye from the total wave aberration in the eye through objective vision optimization. The optical diagnosis module is configured to: a) compute a simulated retinal image under the objectively determined sphero-cylindrical correction by computing a point-spread function from residual aberrations and convolving the computed point-spread function with an acuity chart, where the residual aberrations is computed by subtracting the sphero-cylindrical correction from the total wave aberration; b) display the simulated retinal image on a display device; and c) provide an optical diagnosis through a human-machine interface. The optical diagnosis includes at least one of: c1) determining excess aberrations in the eye, the excess aberrations being defined as a portion of the residual aberrations that are more than high-order aberrations in eyes for normal optics for seeing at least 20/20 with clear vision or for exceptional optics for seeing at least 20/12; c2) ranking an optics of the eye into a plurality of optical grades based on the simulated retinal image; c3) selecting the eye for which high-definition eyeglasses is delivered if the eye has the potential of seeing 20/12 acuity according to the simulated retinal image, wherein the high-definition eyeglasses are made with free-form technology with an incremental step finer than 0.25D for at least a cylinder power CYL; c4) identifying amblyopia or macular diseases based on the simulated retinal image and a best corrected visual acuity for the eye, wherein the best corrected visual acuity is subjectively determined; or c5) choosing an objective refraction for vision correction, the choosing comprising generating a plurality of objective sphero-cylindrical corrections that differ from each other in cylinder power, calculating a plurality of calculated retinal images that correspond to the generated objective sphero-cylindrical corrections, and reviewing the calculated retinal images on the display device.

DETAILED DESCRIPTION

Methods and systems for performing optical diagnosis are provided in which not only visual acuity is assessed, but other optical issues can be determined as well. The methods and systems utilize measurements of residual aberrations to calculate a point-spread function and consequently calculate a simulated retinal image. An optical diagnosis based on the simulated retinal image, which may involve reviewing the simulated retinal image by an operator through a human-machine interface of an optical diagnosis module, determines diagnoses such as excess aberrations, rankings of the patient's optics, feasibility for high-definition eyeglasses, identification of amblyopia or macular diseases, and objective refractions for vision correction. In this disclosure, an operator may be, for example, an optician, an optometrist, or a technician.

Refraction corrections for eyeglasses are typically represented by a spherical power and an astigmatism. In this disclosure, spherical power ("SPH" in the present embodiments) may also be referred to as a focus error or focus power. The astigmatism (AST) includes a cylinder power ("CYL" in the present embodiments) and a cylinder axis ("AXIS" in the present embodiments), where the cylinder axis may also be referred to as a cylinder angle.

Wavefront aberrometers are known to provide objective measurements of all the aberrations in human eyes. An eye's aberrations cause retinal image blur and degrade image quality and visual acuity. Refractive correction for eyeglasses involves the determination of the aberrations in the eye that can be incorporated into corrective eyeglasses.

After obtaining an eye's wave aberrations, which is a 2D function W(x,y) at the pupil plane, one can determine:
1) An objective refractive correction for eyeglasses that can be expressed as an objective spherical power ("SPH_o"), an objective cylinder power ("CYL_o"), and an objective cylinder axis ("AXIS_o").
2) The residual aberrations R(x,y) in the eye when SPH_o and astigmatism (CYL_o, AXIS_o) are completely corrected, i.e., R(x,y)=W(x,y)−SPH−CYL (power, AXIS). Residual aberrations may include coma, spherical aberration, and a host of other aberrations (commonly expressed by Zernike aberrations).
3) Calculated retinal images of an acuity chart from the residual aberrations, from which the potential for the best corrected acuity can be estimated.

Figure 1:
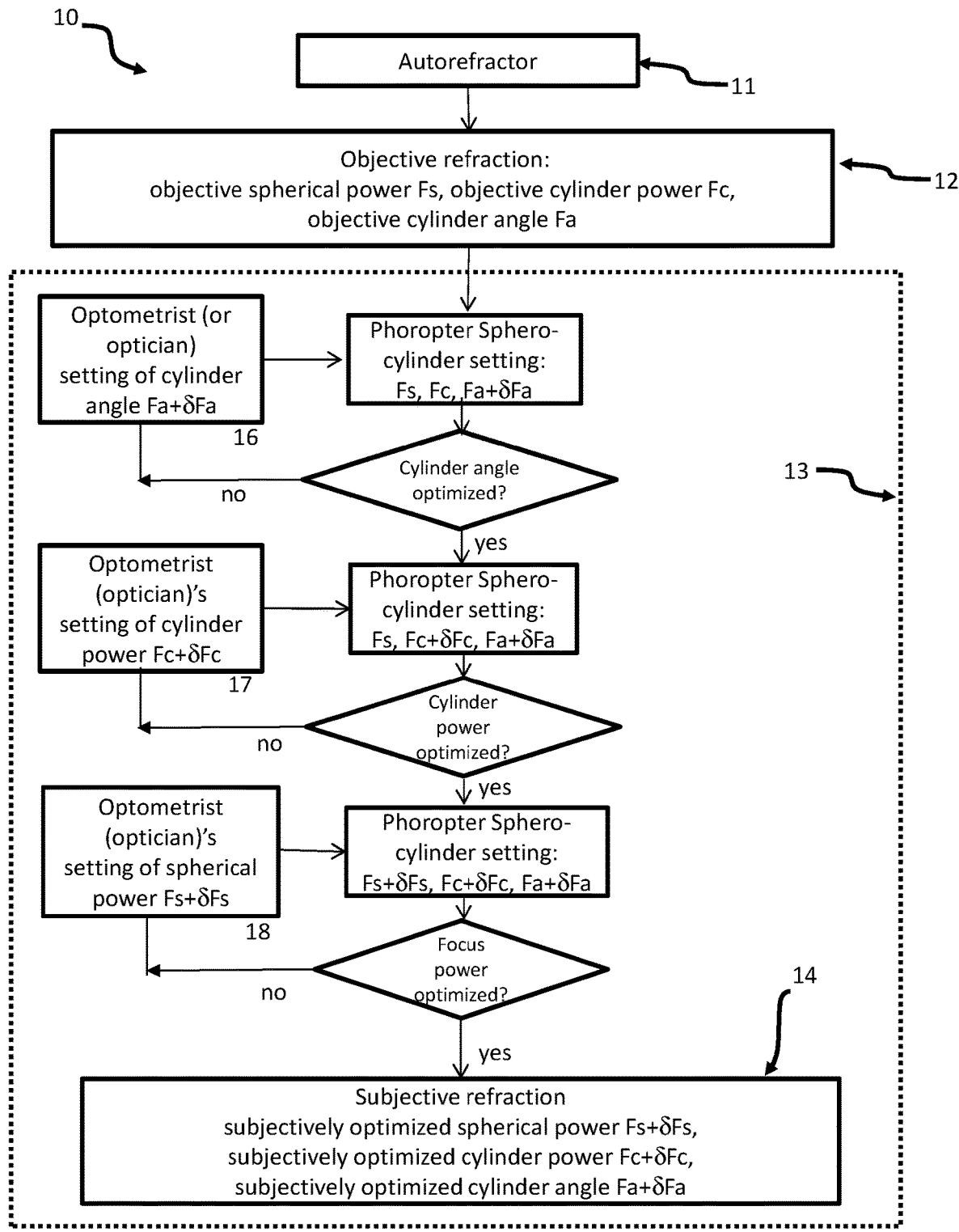
FIG. 1 shows a block diagram of a conventional refraction process.

Wavefront measurements of eye are traditionally performed in low-lit conditions with a large pupil size of 6 mm to 8 mm so that high-order aberrations at pupil periphery are captured. On the other hand, as shown in FIG. 1, prescriptions of eyeglasses are conventionally determined subjectively with a spherical power $F_s+SFS$ (also referred to in this disclosure as SPH_s), a cylinder power $F_c+\delta F_c$ (also referred to in this disclosure as CYL_s), and a cylinder angle $F_a+\delta F_a$ (also referred to in this disclosure as AXIS_s), where the pupil size of the tested eye has a mean value of about 4 mm in the clinical setting with an acuity chart at about 100 cd/m² for the subjective measurements. Optical diagnosis based on traditional wavefront measurements and conventional subjective refraction together is not possible because 1) the cylindrical corrections in subjective refraction (CYL_s, AXIS_s) and objective refraction (CYL_o, AXIS_o) are usually completely different because they are derived using different approaches and under different pupil sizes, and 2) wave aberrations as well as optical quality for a large 6 mm pupil cannot be used to predict subjective acuity or quality of vision during acuity measurements.

The present embodiments overcome issues in traditional wavefront measurement and subjective refraction to make optical diagnoses possible by uniquely 1) making objective cylinder correction (CYL_o, AXIS_o) identical to the prescription cylinder correction, that is replacing (CYL_s, AXIS_s) in the prescription with (CYL_o, AXIS_o), 2) measuring the eye's wave aberration at the same or a similar pupil size at which subjective acuity is measured, and 3) updating the objective spherical power SPH_o with subjective spherical power SPH_s using a high resolution phoropter that can correct cylinder power as fine as 0.01 D, matching the resolution of aberrometers. Under these conditions, optical diagnosis using objectively determined residual aberrations of an eye beyond a sphero-cylindrical correction (SPH_s, CYL_o, AXIS_o) is made possible.

Figure 2:
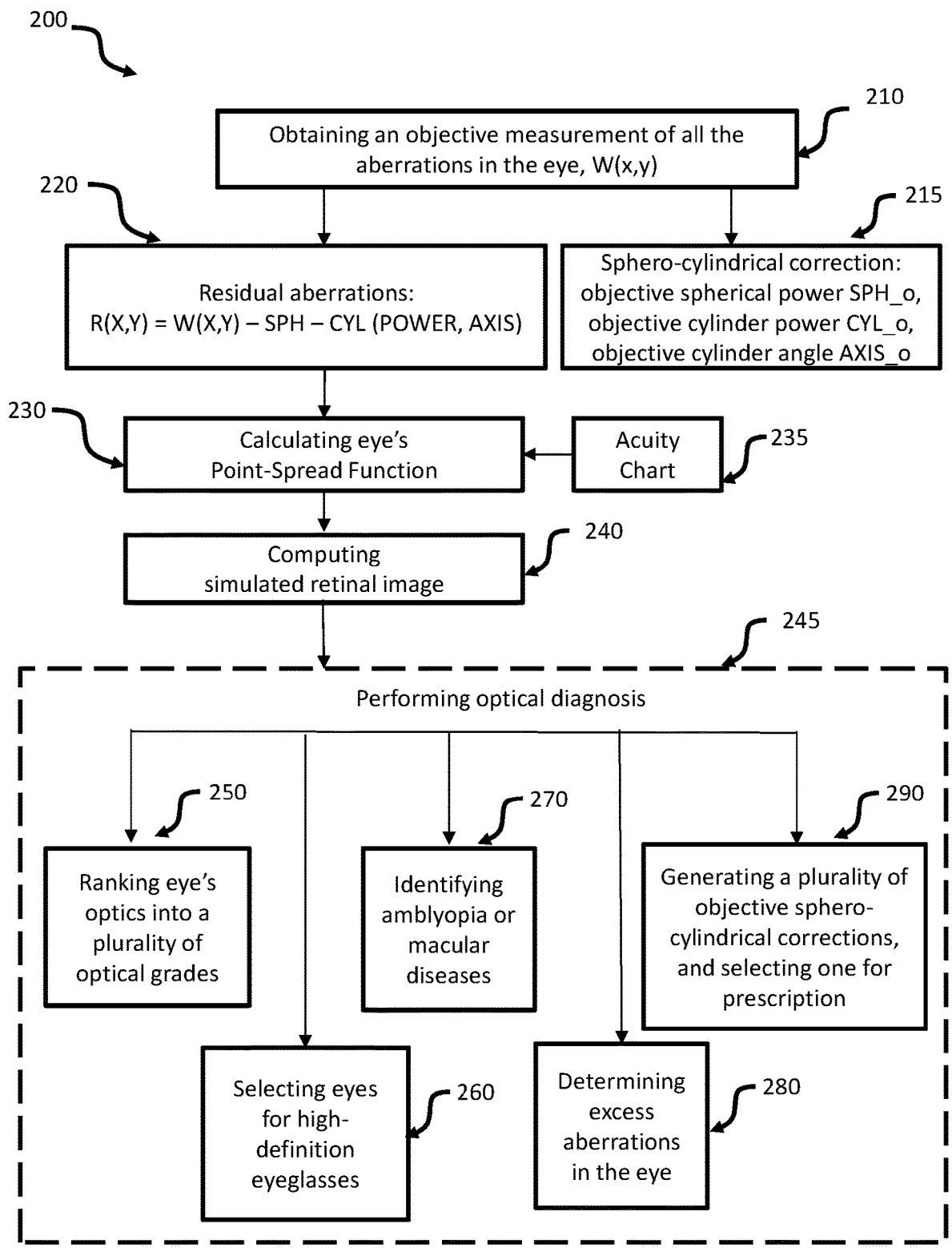
FIG. 2 shows a flow chart of a method of optical diagnosis for eye exams in accordance with some embodiments.

FIG. 2 is a flowchart of a method 200 for optical diagnosis of an eye's optical image quality for eye exams. Step 210 of the method 200 for determining an optical diagnosis involves obtaining an objective measurement of a total wave aberration of an eye of a patient using an objective aberrometer module. The objective measurement does not involve responses from the patient. In some embodiments, the objective aberrometer module uses a lens array or a Hartmann-shack sensor for the measurement of the eye's wave aberration. Objective aberrometers used in the present embodiments can also be constructed in other principles and device configurations such as laser ray tracing, spatially resolved refractometer, Talbot-Moire interferometry, skiascopic phase difference, Tscheming principle, and the like.

The objective wavefront measurement of step 210 includes all the aberrations in the eye. That is, the objective measurement includes a sphero-cylindrical correction of step 215 and residual aberrations of step 220, the sphero-cylindrical correction consisting of an objective spherical power (SPH_o), an objective cylinder power (CYL_o), and an objective cylinder axis (AXIS_o). In some embodiments, the sphero-cylindrical correction is determined by an objective refraction software module from the objective wavefront measurement. The residual aberration R(x,y) is computed by subtracting the sphero-cylindrical correction from eye's total wave aberration W(x,y). The objective prescription (SPH_o, CYL_o, AXIS_o) is targeted to provide the best image quality (i.e., the best retinal image quality possible) for the eye through objective vision optimization. That is, the sphero-cylindrical correction is obtained through objective vision optimization to achieve a best image quality for the eye.

Pupil size of an eye, ranging from about 2 mm outdoors during the day to 6 mm or larger at night, depends on the surrounding light conditions. Visual acuity is measured subjectively in clinical settings. In one embodiment, obtaining an objective measurement of a wave aberration of an eye of a patient in step 210 is performed for the same or similar pupil size for which conventional subjective acuity is measured. Pupil size of the tested eye during wavefront measurements can be controlled in one embodiment by a light source placed in front of the eye. When the light source for pupil control is turned on during wavefront measurements, wavefront measurements will be performed at a similar pupil size for which subjective acuity is measured. The light source for pupil control in wavefront measurement can be calibrated by 1) measuring pupil sizes of a number of eyes when patients view an acuity chart in a standard clinical setting for subjectively measuring acuity when the light source module for pupil size is turned off, 2) measuring pupil sizes of the same eyes when a wavefront measurement of the eyes is performed with the light source turned on and at a number of various intensity levels, and then 3) determining a calibrated intensity level of the light source for pupil control so that the pupil size during the objective wavefront measurement closely matches that of the measured pupil size during subjective acuity measurement when the light source module for pupil control is turned off.

In another embodiment, the wavefront is first measured for a larger pupil size, and the wave aberration of eye during acuity measurement can then be determined by truncating the wavefront at a large pupil size to a smaller pupil size if the pupil size of the eye during acuity can be determined using other methods.

In one embodiment, the objective corrections of SPH_o, CYL_o, and AXIS_o in step 215 are determined by minimizing the residual RMS (Root Mean Square) wavefront error from the objective measurement of a wave aberration of an eye of a patient (W(x,y)). In another embodiment, the objective corrections of SPH_o, CYL_o, and AXIS_o in step 215 are determined through objective vision optimization to achieve a best image quality possible for the eye. This objective vision optimization can be achieved by 1) numerically varying all three parameters of SPH_o, CYL_o, and AXIS_o in a plurality of combinations, 2) calculating an objective retinal image quality for each combination in the plurality of the combinations, and 3) determining a combination of SPH_o, CYL_o, and AXIS_o to achieve the best image quality (i.e., the best objective retinal image quality). The optimization is performed in an automated manner, where the many combinations of SPH_o, CYL_o, and AXIS_o can be computed quickly by a computer processor.

In one embodiment, objective retinal image quality is measured by one or more of the following parameters: a Strehl ratio (peak intensity) of a point-spread function for each combination in the plurality of the combinations, a half-height width of a point-spread function for each combination in the plurality of the combinations, or a modulation transfer function at a spatial frequency. For example, certain spatial frequencies may be used such as 30 cycles/degree (fundamental frequency for 20/20), 60 cycles/degree (fundamental frequency for 20/10), or their variations.

From the residual aberrations of step 220, an eye's point-spread function is calculated in step 230. That is, step 230 involves computing a point-spread function from the residual aberrations. Step 240 of the method 200 involves computing a simulated retinal image of an acuity chart under the sphero-cylindrical correction from the residual aberrations by convolving the computed point-spread function of step 230 with an acuity chart 235. In one embodiment, the acuity chart is a picture with letters of different sizes. The letters can be arranged in rows, where each row represents a different acuity level such as 20/40, 20/30, 20/25, 20/20, 20/16, 20/12, and 20/10. In some embodiments, step 240 may also involve displaying the simulated retinal image on a display device, such as a monitor, to be reviewed by an operator.

Figure 3:
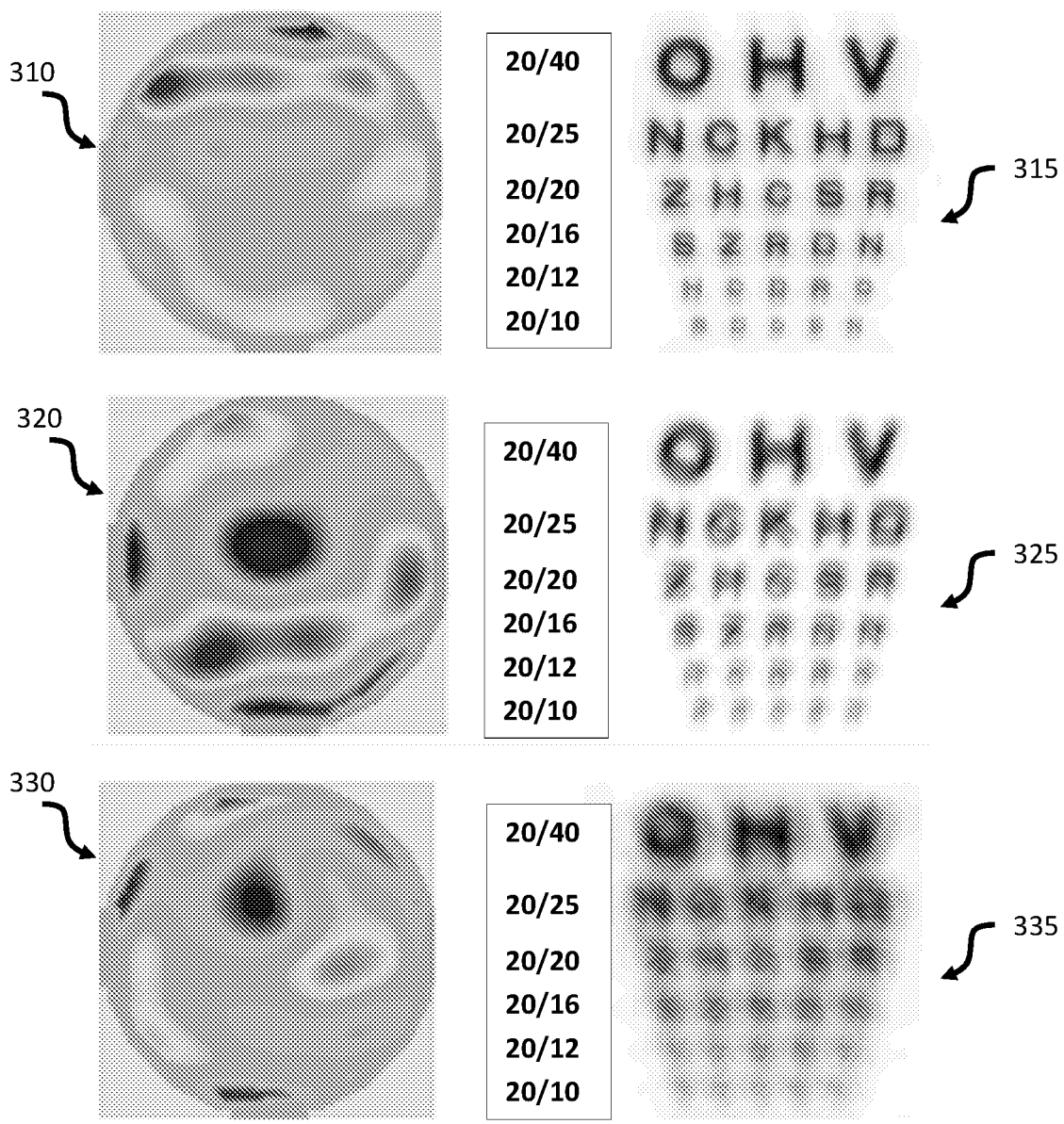
FIG. 3 shows calculated retinal images of three eyes as well as residual aberrations in the eyes that are not correctable by a sphero-cylindrical correction.

FIG. 3 shows examples of residual aberrations (310, 320, 330) and simulated retinal images (315, 325, 335) which are the calculated best retinal images possible under a sphero-cylindrical correction (SPH_o, CYL_o, AXIS_o) for 3 tested eyes. Wavefront maps of the residual aberrations (310, 320, 330) for each eye are shown as 2D maps while the simulated retinal images (315, 325, 335) along with the size of acuity letters for each line are included. The three cases shown in FIG. 3 represent different optical grades of an eye. For the first tested eye, the simulated retinal image 315 is derived from the residual aberrations 310 by first computing the eye's point-spread function from the residual aberrations 310 and then convolving the computed point-spread function with an acuity chart. Simulated retinal image 315 shows exceptionally good vision, such as 20/12 or better. For the second tested eye in FIG. 3, the residual aberration 320 is higher (as indicated by more areas of color gradations than in image 310) which results in the simulated retinal image 325 that indicates lower (worse) visual acuity than the first eye. In the third tested eye, the residual aberration 330 is not only higher than the residual aberrations 310 but also has a specific configuration, having more aberrations in certain areas of the eye than normal eyes. Consequently, the simulated retinal image 335 that is even more blurry than the images 315 and 325.

Returning to FIG. 2, step 245 of the method 200 involves performing an optical diagnosis of the eye's optical image quality based on the simulated retinal image computed in step 240. In some embodiments, the optical diagnosis is performed by an optical diagnosis module, independent of a human operator. For example, the optical diagnosis module can be configured (i.e., programmed) to automatically analyze the simulated retinal image, such as by using computer image analysis, where the simulated retinal image may or may not need to be displayed on a display device. In some embodiments, the optical diagnosis is performed by an optical diagnosis module through a human-machine interface. For example, embodiments may involve performing the optical diagnosis of the eye's optical image quality by an operator in reviewing the simulated retinal image on a display device and then providing feedback of their review through the human-machine interface.

In one embodiment, the optical diagnosis includes step 250 of ranking the eye's optics into a plurality of optical grades based on the simulated retinal image under a spherocylindrical correction (i.e., the objectively-measured spherocylindrical correction of step 215). The plurality of optical grades in accordance with the present embodiments includes a "Class 1 SuperVison Optics" if, based on the simulated retinal images, the operator and/or optical diagnosis module determines that the eye can see 20/12 or better. That is, a ranking of Class 1 is determined if the optics of the tested eyes is good enough for seeing 20/12 or better in at least one of the two eyes of the test subject (e.g. simulated retinal image 351 in FIG. 3). It is estimated that about 60% of the population has excellent optics for 20/12 or better based on a study of more than 60 normal patients that was performed in relation to this disclosure. The plurality of optical grades can also include a "Class 2 Normal Vision Optics" if the operator and/or optical diagnosis module determines, in reviewing the simulated retinal image of an acuity chart, that the eye can see 20/20 or better but cannot see 20/12 letters of the acuity chart. An example of Class 2 vision is simulated retinal image 325 of FIG. 3. It is estimated that a little more than 30% of the population has Class 2 Normal Vision Optics based on the study of more than 60 patients mentioned above. The optical grades can also include a "Class 3 Aberrated Eyes" if the operator and/or optical diagnosis module determines, in reviewing the simulated retinal image of an acuity chart, that the eye cannot see 20/20 letters in the acuity chart or has poor image clarity even though the 20/20 letters are recognizable. An example of Class 3 optical grade is simulated retinal image 335 of FIG. 3.

There are at least three advantages of ranking an eye's optical quality into different optical grades objectively in the present disclosure.

First, ranking an eye's optical quality into different grades can help to identify eyes in which the vision standard can be raised from normal 20/20 vision to supernormal vision of 20/12 or better with free-form high-resolution lenses. Free-form lenses are custom designed to eliminate lens aberrations for different viewing directions and can be manufactured at an incremental step (i.e., resolution or measurement interval) much finer than conventional 0.25D increments. For example, free-form lenses can be fabricated with a precision of 0.01D in theory and 0.05D in practice for SPH and CYL. However, free-form lenses are significantly more expensive than conventional lenses at incremental steps of 0.25D. In the present disclosure, High-Definition (HD) vision using free-form lenses can beneficially be targeted to eyes with "Class 1 SuperVision Optics." Realizing exceptional vision or true HD vision of 20/12 or better, which is far superior to the standard of 20/20 acuity, for these Class 1 eyes is achieved in some embodiments by correcting optical quality of human eyes for 20/12 optics together with perfectly designed free-form lenses, which are free from lens aberrations. More importantly, offering HD vision only to the selected eyes with "Class 1 SuperVision Optics" prevents vendors from selling expensive and custom free-form lenses to patients whose eyes will not benefit from high-definition vision, such as patients with "Class 2 Normal Vision Optics" or "Class 3 Aberrated Eyes." Because the aberrations in these eyes (class 2 and class 3) are more significant than the lens aberrations, eyes under "Class 2 Normal Vision Optics" and "Class 3 Aberrated Eyes" can at best see 20/20 or 20/16 no matter how perfect the lenses are made. Therefore, these patients will be better served with less expensive lenses instead of buying expensive custom-made free-form lenses.

This embodiment of an optical diagnosis in which an operator selects an eye that is suitable for high-definition eyeglasses is shown in step 260 in FIG. 2. The selected eye for which high-definition eyeglasses is to be delivered is shown to have exceptional optical quality for achieving 20/12 acuity according to the simulated retinal image such as those ranked as Class 1 SuperVision Optics (e.g., retinal image 315 of FIG. 3). The high-definition eyeglasses for these selected patients are made with free-form technology with an incremental step of the lens diopter values finer than 0.25D, such as 0.01D. Thus, in some embodiments, step 260 involves selecting the eye for which high-definition eyeglasses is delivered if the eye has exceptional optical quality for potentially achieving 20/12 acuity according to the simulated retinal image, wherein the high-definition eyeglasses are made with free-form technology with an incremental step finer than 0.25D for at least a cylinder power CYL.

Figure 4:
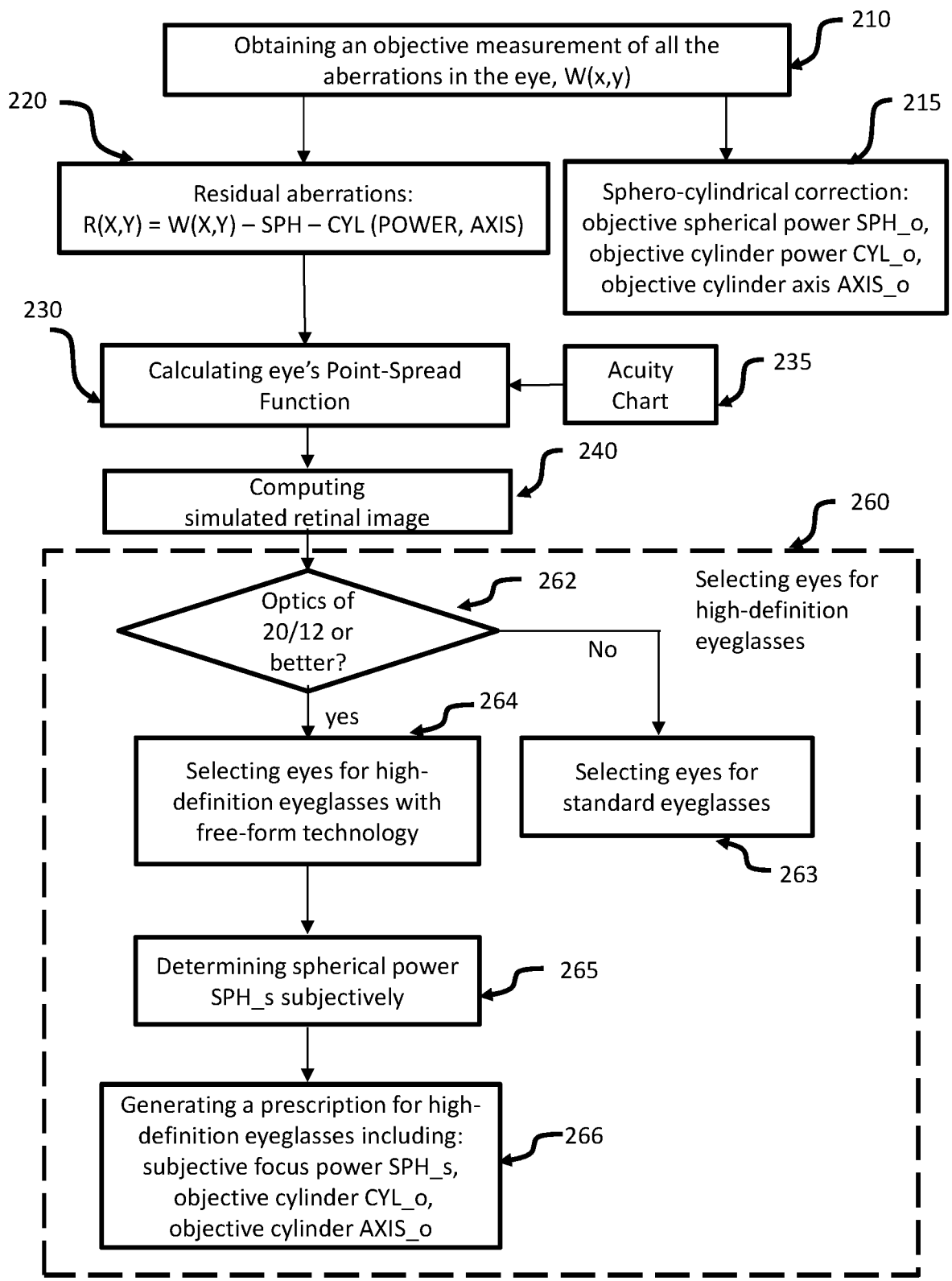
FIG. 4 shows a flow chart of a method of optical diagnosis for selecting eyes for high-definition eyeglasses based on simulated retinal images in accordance with some embodiments.

Further details of selecting patients for high-definition eyeglasses (step 260) are shown in the embodiment of FIG. 4. In step 262 an optical diagnosis module determines, by reviewing the simulated retinal images, if the eye's optics of the test subject have the potential for visual acuity of 20/12 or better. In one embodiment, the optical diagnosis is provided through a human-machine interface of the optical diagnosis module, in which an operator can review and input a determination about the simulated retinal image. In another embodiment, the optical diagnosis modules digitally analyzes the simulated retinal image using image analysis software to determine the clarity of the letters. If the optics of the eye (i.e., clarity of vision produced by the cornea, pupil and lens of the eye) are not determined to be 20/12 or better in step 262, the eyes are selected to receive standard eyeglasses in step 263. If the optical diagnosis module and/or operator confirms that the eye's optics are good enough for 20/12 vision in step 262, the eyes are selected for high-definition in step 264 and the subjective spherical power SPH_s is subjectively determined in step 265 using devices such as a phoropter, where SPH_s replaces the objective SPH_o in the eyeglass prescription. In step 266, the lenses of high-definition eyeglasses are prescribed for free-form designs with a generated prescription that includes the spherical power SPH_s, cylinder power CYL_o, and cylinder axis AXIS_o. That is, the high-definition eyeglasses are custom manufactured using the free-form technology using a prescription that includes the subjective spherical power SPH_s, the objective cylinder power CYL_o, and the objective cylinder axis AXIS_o, where the subjective spherical power SPH_s replaces the objective spherical power SPH_o and is subjectively determined using a phoropter.

A second advantage of ranking an eye's optical quality into different grades is to help in identifying amblyopia or macular disease. Accordingly, in some embodiments the optical diagnosis of an eye's image quality further includes identifying amblyopia or macular diseases based on the simulated retinal image and a best corrected visual acuity for the eye, as shown in step 270 of FIG. 2, where the best corrected visual acuity is subjectively determined.

Figure 5:
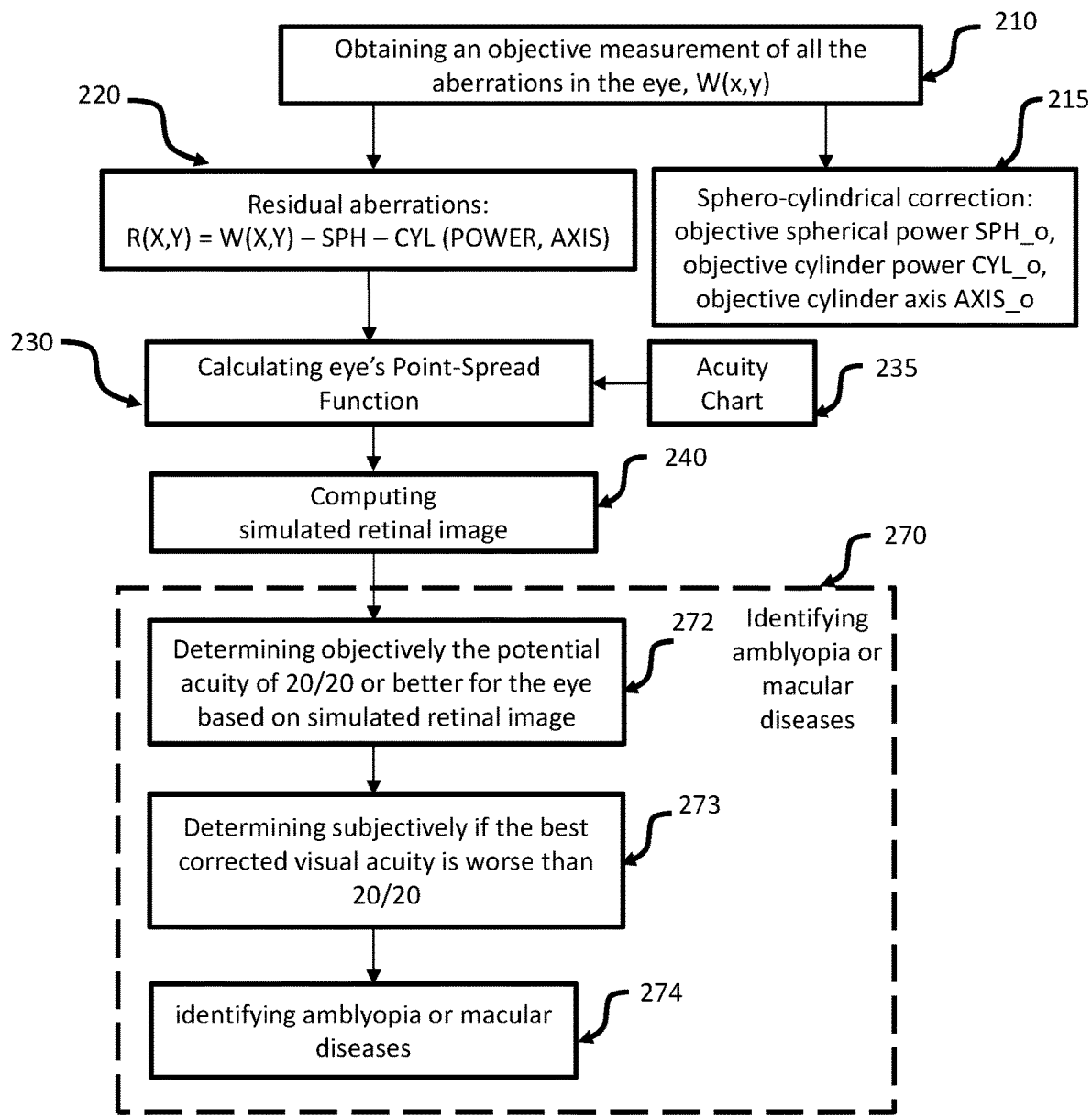
FIG. 5 shows a flow chart of a method of optical diagnosis for identifying amblyopia or macular diseases based on simulated retinal images and the best corrected visual acuity for the eye in accordance with some embodiments.

FIG. 5 shows details of one embodiment of step 270 where identifying amblyopia and macular diseases is confirmed when 1) the best corrected visual acuity of the eye is worse than 20/20, and 2) the optics of the eye is found to be normal or capable of seeing 20/20 or better, which includes eyes classified as Class 1 SuperVision Optics or Class 2 Normal Vision Optics. First, in step 272 the potential for the optics of the eye to have an acuity of 20/20 or better is determined objectively by an optical diagnosis based on the objectively calculated simulated retinal images. In one embodiment, the optical diagnosis is provided through a human-machine interface of the optical diagnosis module, in which an operator can review and input a determination about the simulated retinal image. Examples of potential eyes for acuity of 20/20 or better are those classified as Class 1 SuperVision Optics or Class 2 Normal Vision Optics (see retinal images 315 and 325 in FIG. 3). In step 273, the best corrected visual acuity of the tested eye is determined subjectively. If the subjective measurement of the best corrected acuity is reported to be worse than the 20/20 standard, such as 20/40 or 20/80, this discrepancy between the eye's optics (determined objectively) and patient's subjective acuity can be used for identifying amblyopia and macular diseases of an eye by the optical diagnosis module and/or the operator in step 274. The best corrected visual acuity in step 273 is determined subjectively using devices such as a phoropter.

A third advantage of ranking an eye's optical quality into different grades is to identify eyes with poor optics for determining excess aberrations for vision diagnosis as shown in step 280 of FIG. 2. Excess aberrations are defined as a portion of the eye's residual aberrations that are more than the amount of typical high-order aberrations in eyes for normal optics for seeing at least 20/20 with clear vision, or for exceptional optics for seeing at least 20/12.

Figure 6:
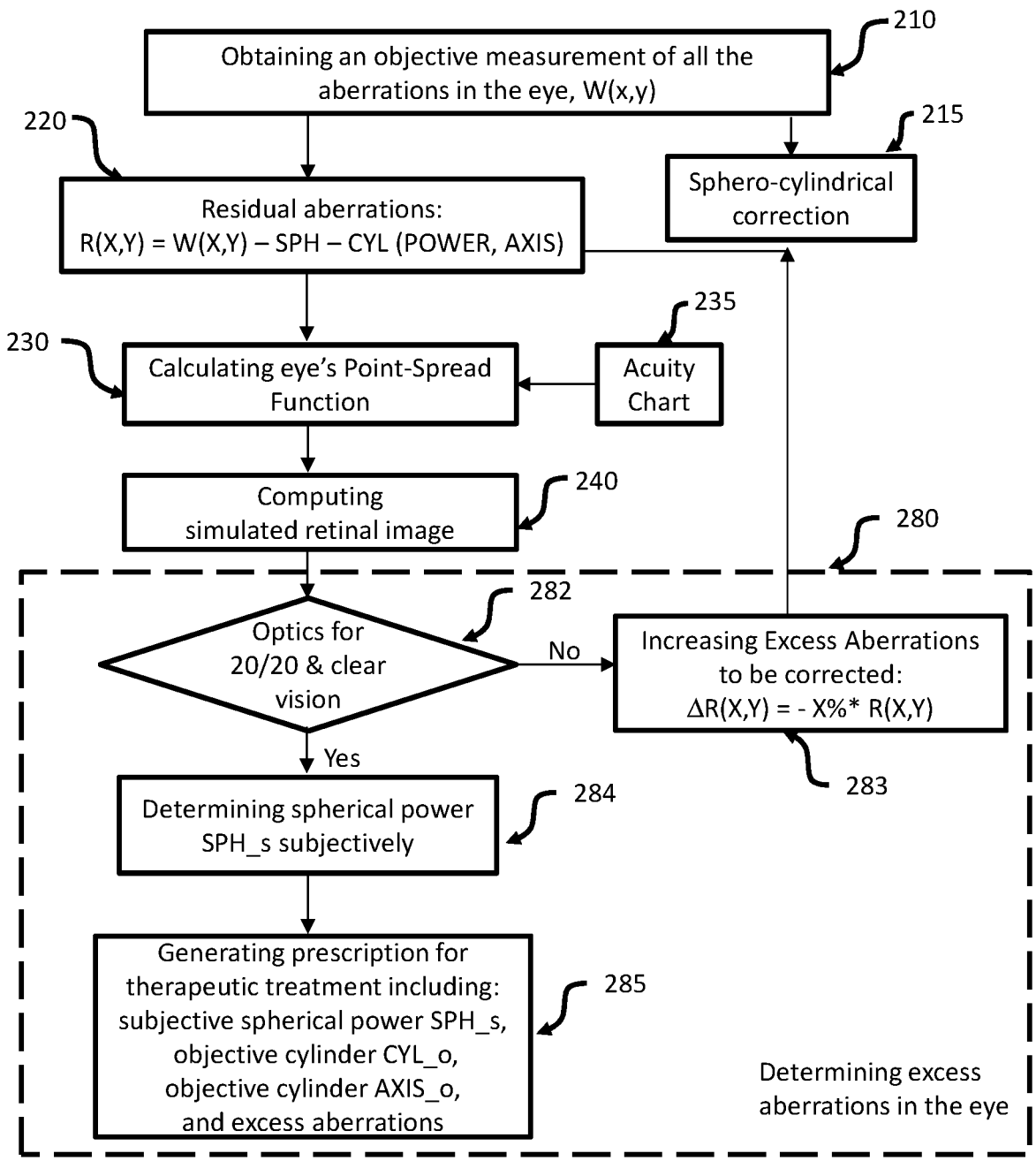
FIG. 6 shows a flow chart of a method of optical diagnosis for determining excess aberrations in the eye in accordance with some embodiments.

An example embodiment of details involved in step 280 is shown in FIG. 6. Determining excess aberrations in the eye under a sphero-cylindrical correction of step 280 is performed in step 283 through either reducing the residual aberrations in the eye by a percentage X % or increasing excess aberration ($\Delta R = -X\% * R(x,y)$) to be corrected in the simulation. In some embodiments, step 283 may be performed by an optical diagnosis module, where the optical diagnosis module may generate percentage values to use in the calculation. In some embodiments, the optical diagnosis is provided through a human-machine interface of the optical diagnosis module where the reduction of residual aberrations or increasing of excess aberrations are controlled by the operator through a human-machine interface such as, but not limited to, a keyboard or a computer mouse. The revised residual aberrations are used in step 220, then a new point-spread function is calculated in step 230, and then step 240 for computing a new simulated retinal image of the acuity chart 235 is performed. The modified residual aberrations used in these recalculations are equal to $(1-X)*R(x, y)$, the original residual aberration in step 220 in FIG. 6 (from the objective measurement of step 210) minus the reduced residual aberrations or minus the increased excess aberration from step 283, where the reduced residual aberration or increased excess aberration may be controlled by the operator. That is, in some embodiments the method involves computing a new simulated retinal image of the acuity chart from modified residual aberrations that equal to the residual aberrations minus the reduced residual aberrations. The loop of steps 283, 220, 230 and 240 are repeated until conditions are met in decision step 282. That is, step 280 of the method 200 involves stopping the reducing of the residual aberrations in the eye when the displayed new simulated retinal image of the acuity chart enables the eye to see at least 20/20 with clear vision. In some embodiments, step 280 involves stopping to further reduce residual aberrations in the eye until the optical diagnosis module and/or operator determines in decision step 282 that the new simulated image of an acuity chart enables the eye to see at least 20/20 letters with clear vision, or to see 20/12 letters (supernormal vision). In some embodiments, the simulated retinal images are displayed and step 280 involves stopping the reducing of the residual aberrations in the eye when the operator determines that the displayed new simulated retinal image of the acuity chart enables the eye to see at least 20/20 with clear vision. In further embodiments, step 283 may involve specifying the excess aberrations as the magnitude of the reduced residual aberrations.

Figure 7:
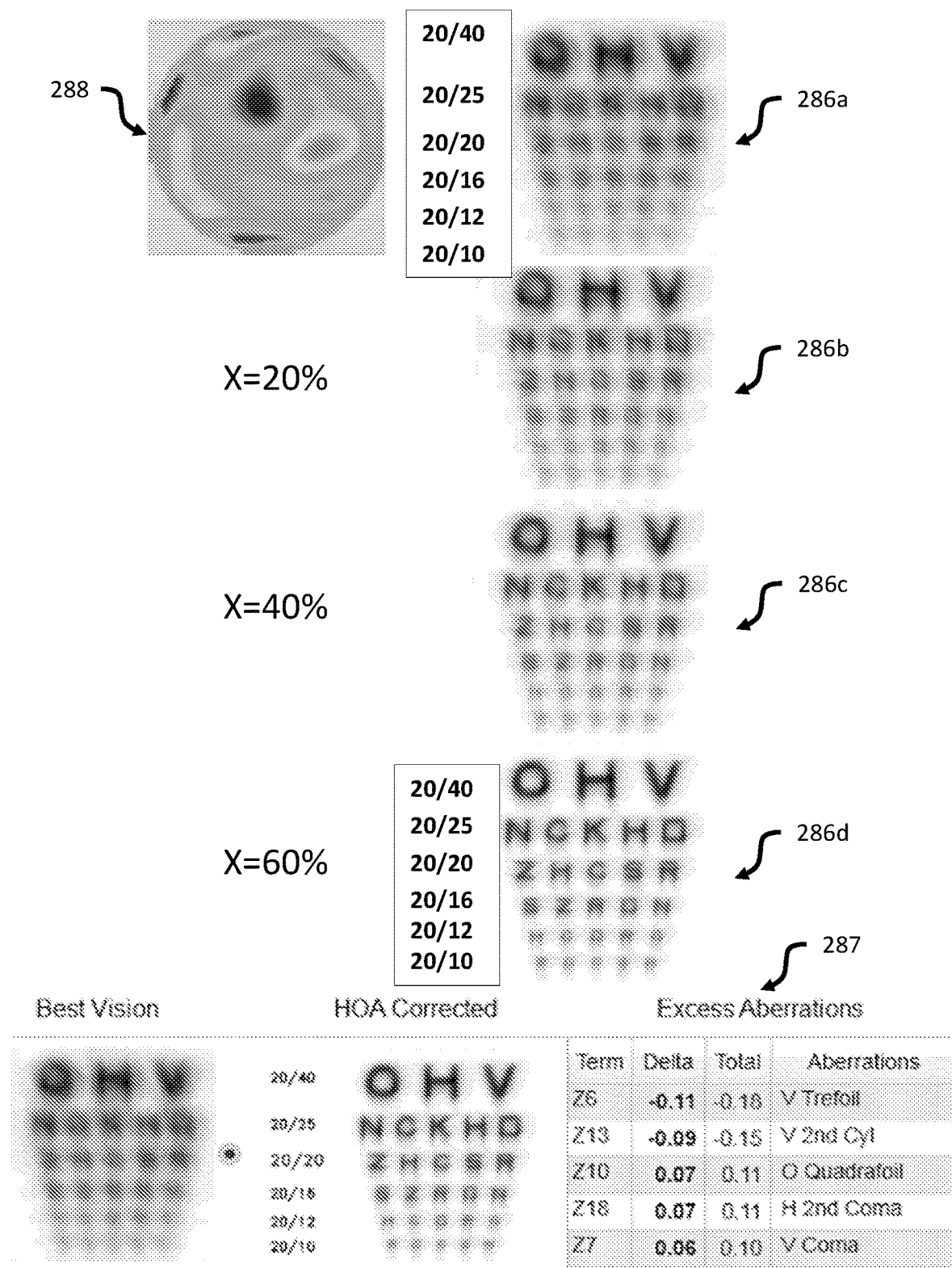
FIG. 7 shows an example of determining excess aberrations in the eye.

FIG. 7 shows examples of determining excess aberrations in one tested eye under a sphero-cylindrical correction, according to the method 200 of FIG. 6. First, the original residual aberrations (image 288) and an initial calculated best retinal image possible (simulated retinal image 286a) from the original residual aberrations under a sphero-cylindrical correction (SPH_o, CYL_o, AXIS_o) for one tested eye is shown. It can be seen that neither optics for 20/20 nor clear vision are met in the simulated retinal image 286a (per decision step 282 of FIG. 6). Consequently, the operator and/or optical diagnosis module determines the excess aberration of the tested eye per step 283 of FIG. 6. In this example of FIG. 7, percentages of X=20%, 40%, and 60% of the total residual aberrations are used, which may be generated by the optical diagnosis module or may be input by an operator through a human-machine interface. The optical diagnosis module calculates and optionally displays simulated retinal images 286b, 286c, and 286d for the percentages X=20%, 40%, and 60%, respectively, for the same tested eye. It is shown in FIG. 7 that when X=60%, the calculated retinal image 286d is clear enough for seeing letters of 20/12 (the second line from the bottom of the acuity chart). Thus, the high-order aberration (HOA) corrected percentage of 60% is used. Excess aberrations of the tested eye are specified (i.e., identified, as shown in chart 287 of FIG. 7) as a portion of the largest aberrations, measured by Zerhike coefficients, in the reduced residual aberrations. In this example of FIG. 7, the excess aberrations of chart 287 are identified by the five largest Zernike terms: Z6 (Vertical Trefoil), Z13 (Vertical Secondary Astigmatism), Z10 (Oblique Quadrafoil), Z18 (Vertical Secondary Coma), Z7 (Vertical Coma), with a magnitude of −0.11 microns, −0.09 microns, 0.07 microns, 0.07 microns, and 0.06 microns, respectively for the case of X=60%. Details about Zernike aberrations can be found in ANSI Z80.28-2017: Ophthalmics—Methods of Reporting Optical Aberrations of Eyes. In some embodiments, the number of aberration terms that are considered to be the largest aberration terms is equal to or less than 5.

In yet another embodiment, optical diagnosis of the eye's image quality further includes generating a prescription for therapeutic treatment of determined excess aberrations in addition to a conventional sphero-cylindrical correction using surgical lasers or eyeglasses (step 285 of FIG. 6). The prescription includes a subjective spherical power SPH_s, a cylinder power CYL_o, a cylinder axis AXIS_o, and the determined excess (high-order) aberrations. The subjective spherical power SPH_s replaces the objective spherical power SPH_o (step 284 in FIG. 6) and is subjectively determined using devices such as a phoropter.

Objective vision optimization solutions from an eye's wave aberration are mostly unique. That is, deviations from the optimized values of an objective sphero-cylindrical correction of spherical power SPH_o, cylinder power CYL_o, and cylinder angle AXIS_o for a given wave aberration measurement of an eye leads to significant degradation in optical quality. However, objective vision optimization for highly aberrated eyes can be more complicated to achieve, in that multiple optimized solutions can be calculated where large changes in the optimized values will not cause significant degradation to optical image quality. For example, high-order aberrations in tested eyes can lead to 1) objective image quality such as a Strehl Ratio that only changes slightly even when the cylinder power changes significantly, e.g. more than 1.0D, or 2) images with highest contrast that are also accompanied with multiple images. These high-order aberrations lead to complications in objective vision optimization from the eye's wave aberration.

To solve this issue of objective vision optimization which can be complex in the case of highly aberrated eyes, optical diagnosis of an eye's image quality further includes generating a plurality of objective sphero-cylindrical corrections (step 290 of FIG. 2) as well as computing their corresponding calculated retinal images for the generated objective sphero-cylindrical corrections. The retinal images can then be reviewed and an objective refraction chosen for vision correction. In some embodiments, the reviewing of the simulated retinal images may be performed by an optical diagnosis module, without input from an operator. In other embodiments, the plurality of calculated retinal images can be displayed for reviewing by an operator, where the operator then provides a diagnosis through a human-machine interface of the optical diagnosis module. That is, in some embodiments the optical diagnosis includes choosing an objective refraction for vision correction, the choosing comprising generating a plurality of objective sphero-cylindrical corrections that differ from each other in cylinder power, displaying and calculating a plurality of calculated retinal images that correspond to the generated objective sphero-cylindrical corrections, and reviewing the displayed plurality of calculated retinal images. Details of step 290 of FIG. 2 are provided in FIG. 8. The plurality of objective sphero-cylindrical corrections differ from each other at least in cylinder power. This use of multiple objective sphero-cylindrical corrections is particularly useful for eyes with significant high-order aberrations when objective vision optimization from the eye's aberrations must make a compromise between retinal image contrast, multiple images, and image distortions.

Figure 8:
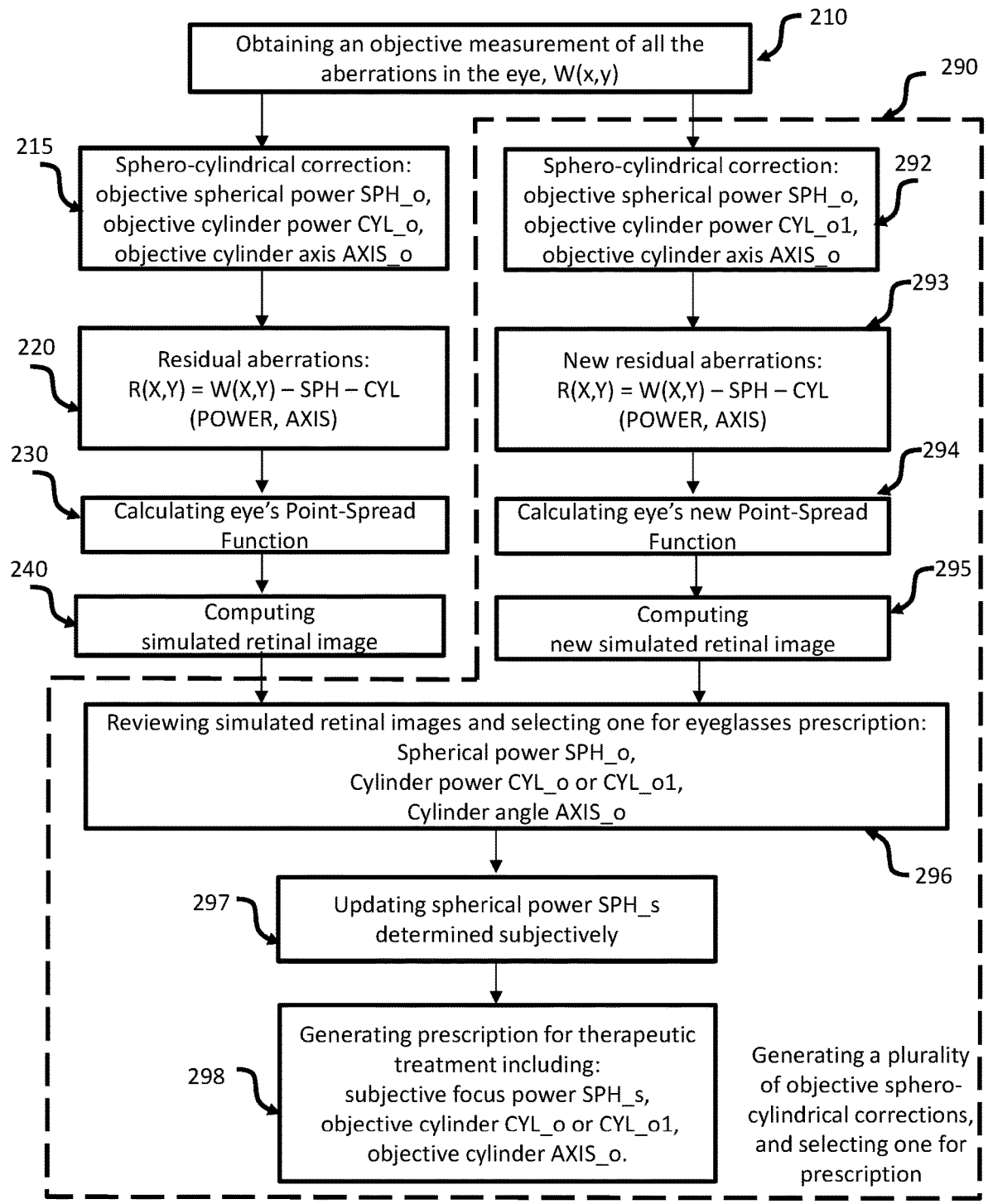
FIG. 8 shows a flow chart of a method of optical diagnosis for obtaining objective refraction by generating a plurality of objective sphero-cylindrical corrections as well as displaying their corresponding calculated retinal images.

In one embodiment (step 290 of FIG. 8), in addition to the best optimized sphero-cylindrical correction of spherical power SPH_o, cylinder power CYL_o, and cylinder angle AXIS_o of step 215 as obtained by the objective measurement of step 210, another sphero-cylindrical correction with different cylinder power CYL_o1 is generated in step 292 of FIG. 8, from which a new residual aberration in step 293, a new point-spread function in step 294, and a new simulated retinal image in step 295 can be calculated. An operator and/or an optical diagnosis module will review (i.e., analyze) the original calculated retinal image of step 240 and the new simulated retinal image of step 295, and select one image in step 296 for the best objective refraction based on a comparison between the two images of image contrast, appearance of acuity letters, and/or magnitude of cylinder power.

Once CYL_o or CYL_o1 is selected by an operator or by an optical diagnosis module based on reviewing retinal images from a plurality of objective refractions in step 296, the optical diagnosis for eye's optical quality further includes generating a prescription for eyeglasses that includes a spherical (i.e., focus) power SPH_s in step 297 that replaces the spherical power SPH_o, and a cylinder power and a cylinder axis that are chosen from the plurality of objective sphero-cylindrical corrections in step 298. The cylinder power may be CYL_o or CYL_o1, and the cylinder axis (i.e., angle) is AXIS_o. The spherical power SPH_s is subjectively determined in step 297 using a device such as a phoropter.

Figure 9:
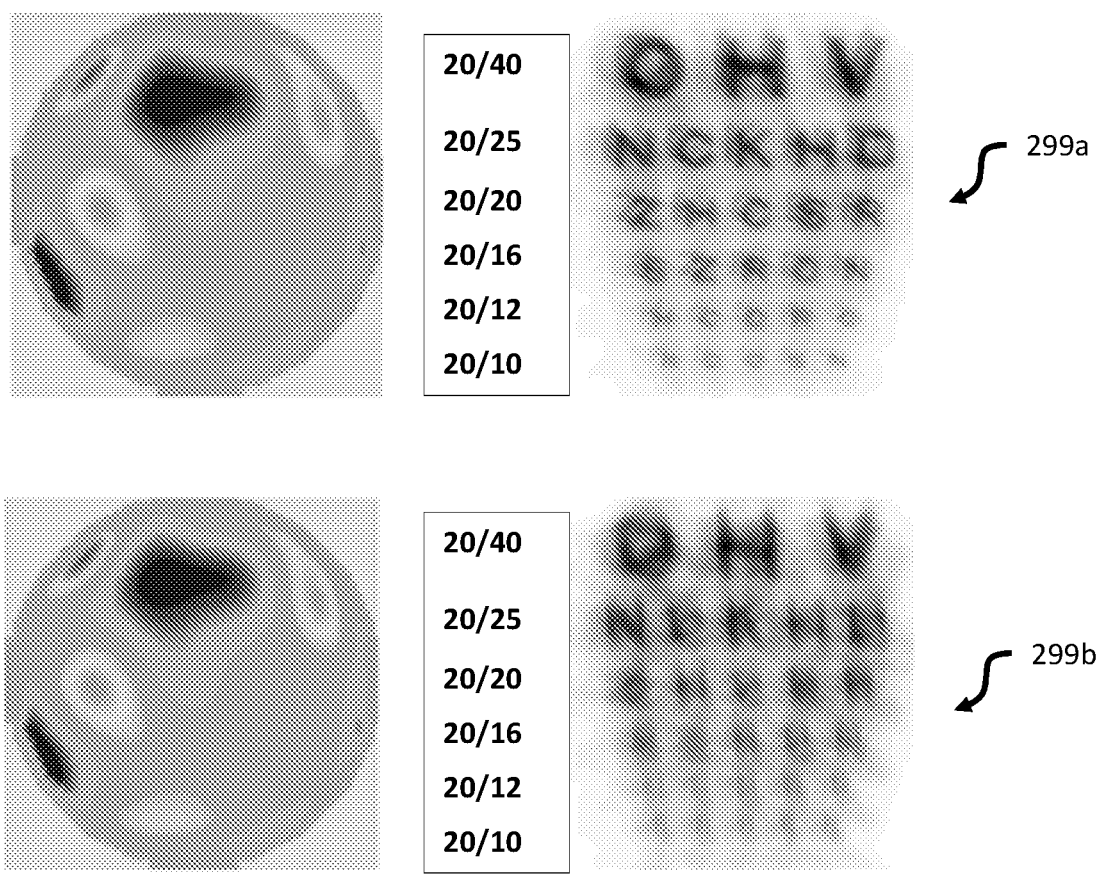
FIG. 9 shows an example of residual wavefront map as well as calculated retinal image for two objective sphero-cylindrical corrections.

FIG. 9 shows an example of calculated (i.e., simulated) retinal images 299a and 299b for two objective corrections with different cylinder powers: CYL_o=−4.5D (for image 299a) and CYL_o1=−3.5D (for image 299b) from the measured wave aberrations in the eye. From the displayed images, operators may provide feedback to the optical diagnosis module for the selection of objective cylinder power, such as through a human-machine interface. In this example of FIG. 9, the operator would choose CYL_o based on image 299a due to the clearer acuity letters compared to image 299b.

In another embodiment, numerical computation for optical diagnosis of eye's optical quality is performed through cloud computing.

Figure 10:
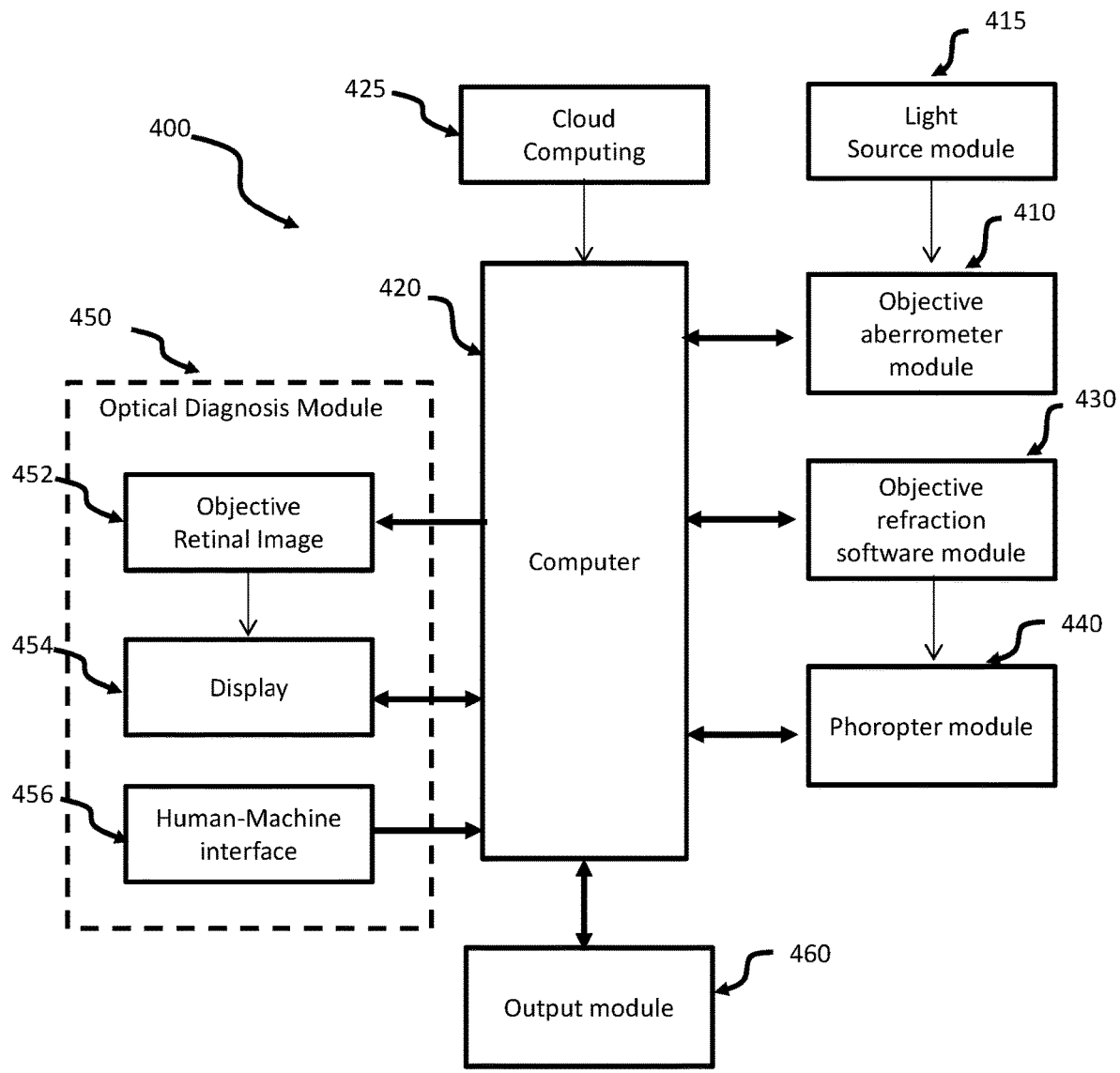
FIG. 10 shows a block diagram of a system of optical diagnosis for eye exams in accordance with some embodiments.

FIG. 10 is a block diagram of a system 400 for optical diagnosis for eye exams, in accordance with some embodiments. System 400 includes an objective aberrometer module 410 configured to obtain an objective measurement of a total wave aberration of an eye of a patient, or wave aberration in the eye. The total wave aberration includes all aberrations in the eye such as spherical power (i.e., focus error) (SPH_o), astigmatism (CYL_o, and AXIS_o), and residual aberrations beyond the sphero-cylindrical correction. The objective measurement does not involve responses from the patient. In one embodiment the objective aberrometer module 410 includes 1) a wavefront sensor for measuring a wavefront, and 2) an optical relay for reproducing the wavefront from the eye to the wavefront sensor. A computer 420 is connected to the aberrometer module 410 hardware for processing the data from the wavefront sensor and generating a wave aberration of a tested eye. Computer 420 can be any electronic processor that is capable of receiving, storing, and calculating data.

In some embodiments, the objective aberrometer module 410 uses a principle or device including but not limited to a Hartmann-shack sensor, laser ray tracing, spatially resolved refractometer, Talbot-Moire interferometry, skiascopic phase difference, Tscheming principle, and the like.

System 400 includes an objective refraction software module 430 configured to determine a sphero-cylindrical correction from the measured total wave aberration in the eye. The objective sphero-cylindrical correction includes an objective spherical power (SPH_o), an objective cylinder power (CYL_o) and an objective cylinder axis (AXIS_o). The objective refraction software module 430 may be part of or separate from the objective aberrometer module 410. The cylinder power is measured by the objective aberrometer module 410 in an increment finer than 0.25D. Because objective aberrometers are very precise, the objective cylinder power is typically in an increment of 0.01D. Consequently, the sphero-cylindrical correction determined by the objective refraction software module 430, using the aberrations measured by the objective aberrometer module 410, are very precise.

In one embodiment, the objective corrections of SPH_o, CYL_o, and AXIS_o are determined by minimizing the residual RMS (Root Mean Square) wavefront error from the objective measurement of a wave aberration of an eye of a patient (W(x,y)).

In another embodiment, the objective correction of SPH_o, CYL_o, and AXIS_o is determined through objective vision optimization to achieve a best image quality for the eye. That is, the sphero-cylindrical correction achieves a best image quality for the eye from the total wave aberration in the eye through objective vision optimization. This can be achieved by 1) numerically varying SPH_o, CYL_o, and AXIS_o in a plurality of combinations, 2) calculating retinal image quality objectively for each of the combinations, and 3) determining one combination of SPH_o, CYL_o, and AXIS_o with their corrections to achieve the best objective retinal image quality.

In one embodiment, objective retinal image quality is measured by one or more of the following parameters: Strehl ratio (peak intensity) of a point-spread function, or the half-height width of a point-spread function, or a modulation transfer function at certain spatial frequencies such as 30 cycles/deg (fundamental frequency for 20/20), 60 cycles/deg (fundamental frequency for 20/10), or variations of these frequencies.

System 400 also includes optical diagnosis module 450 that is in communication with computer 420. The optical diagnosis module is configured for computing an eye's objective retinal image 452 of an acuity chart (i.e., a simulated retinal image) under the objectively determined sphero-cylindrical correction by computing a point-spread function from the residual aberrations and convolving the computed point-spread function with an acuity chart. The residual aberration equals to the total wave aberration subtracting out the determined sphero-cylindrical correction. The acuity chart in one embodiment is a picture with acuity letters of different sizes such as 20/40, 20/30, 20/25, 20/20, 20/16, 20/12, 20/10. The optical diagnosis module is also configured for displaying the calculated (i.e., simulated) retinal image on a display device 454, and providing an optical diagnosis through a human-machine interface 456. The simulated retinal image is used for performing optical diagnosis of the eye's optical quality by an operator, who reviews the simulated retinal image of the acuity chart on a display device.

The display device 454 may be, for example, a computer screen, an electronic tablet, or other viewing monitor that is either physically incorporated with or is a separate component from the wavefront measurement aberrometer (i.e., objective aberrometer module 410).

The human-machine interface 456 is connected to the computer 420 for an operator to perform optical diagnosis based on reviewing the calculated retinal images on a display 454. The human-machine interface can be, for example, a computer mouse, a keyboard, a touching device (e.g., a touch screen), a voice-controlled device, or other devices that enable a human to input information into an electronic device.

The optical diagnosis performed by the optical diagnosis module 450 includes at least one of the following: a) determining excess aberrations in the eye under a sphero-cylindrical correction where the excess aberrations are determined as a portion of the eye's residual aberrations that are more than the amount of typical high-order aberrations in eyes for normal optics to see at least 20/20 with clear vision, or to see 20/12 or better for exceptionally good optics; and where the sphero-cylindrical correction offers the best retinal image quality possible with the correction of a spherical power, a cylinder power with a cylinder axis; b) ranking an eye's optics into a plurality of optical grades based on simulated retinal images under a sphero-cylindrical correction; c) selecting eyes for delivering high-definition eyeglasses based on simulated retinal images under a sphero-cylindrical correction, where the selected eye is shown to have exceptionally good quality for achieving 20/12 acuity according to the simulated retinal image, and the high-definition eyeglasses are made with free-form technology with an incremental step finer than 0.25D for at least cylinder power CYL; d) identifying amblyopia or macular diseases based on simulated retinal image and the best corrected visual acuity for the eye, where the best corrected visual acuity is subjectively determined using correction devices such as a phoropter; or e) generating a plurality of objective sphero-cylindrical corrections as well as displaying their corresponding calculated retinal images on a display device for the generated objective sphero-cylindrical corrections so that operators can review the displayed retinal images and choose an objective refraction as the objective vision optimization. The plurality of objective sphero-cylindrical corrections differ from each other at least in the cylinder power.

In one embodiment, determining excess aberrations in the eye under a sphero-cylindrical correction is performed through the human-machine interface 456 through a process involving: a) reducing the residual aberrations in the eye by a percentage, b) computing and displaying, by the optical diagnosis module, a new simulated retinal image of the acuity chart from a modified residual aberrations that equals to the original residual aberrations minus the reduced residual aberration controlled by the operator, c) stopping to further reduce residual aberrations in the eye when the operator determines that the displayed new simulated retinal image of an acuity chart enables the eye to see 20/20 with clarity or see 20/12 letters for exceptional vision, and then d) specifying the excess aberrations as a magnitude of the reduced residual aberrations controlled by the operator.

In another embodiment, the excess aberrations are specified as some of the largest aberration terms in the reduced residual aberrations.

In yet another embodiment, ranking an eye's optics into a plurality of optical grades under a sphero-cylindrical correction includes rankings of: 1) "Class 1 SuperVison Optics" if the operator determines through the human-machine interface 456, in reviewing simulated retinal images of an acuity chart on a display device, that the tested eyes can see 20/12 or better, 2) "Class 2 Normal Optics" if the operator determines, in reviewing simulated retinal images of an acuity chart on a display device, that the tested eyes can see 20/20 or better but cannot see 20/12 or better, 3) "Class 3 Aberrated Eyes" if the operator determines, in reviewing simulated retinal images of an acuity chart on a display device, that the tested eyes cannot see letters in the line of 20/20 or has poor clarity even though letters of 20/20 is recognizable.

In one embodiment, system 400 also includes a light source module 415 for pupil size control during the objective measurement; that is, the wavefront measurement of an eye. The light source module for pupil size control is configured to be placed in front of the eye and may be, for example, an incandescent bulb, or light emitting diodes. Wavefront measurements of the eye, when the light source module is turned on, will be performed at a similar pupil size for which subjective acuity is measured. Intensity of the light source module for pupil size control can be calibrated to a pupil size for which conventional subjective acuity is measured. For example, the light source module may be calibrated by 1) measuring pupil sizes of a number of eyes when patients view an acuity chart in a standard clinical setting for subjectively measuring acuity when the light source module for pupil size is turned off, 2) measuring pupil sizes of the same eyes when a wavefront measurement of the eyes is performed with the light source module turned on and at a number of various intensity levels, and then 3) determining a calibrated intensity level of the light source module for pupil control so that the pupil size during the objective wavefront measurement closely matches that of the measured pupil size during subjective acuity measurement when the light source module for pupil control is turned off. In some embodiments, the system 400 includes a light source module 415 for pupil size control during a wavefront measurement of the objective measurement, wherein the light source module for pupil size control is placed in front of the eye and is calibrated so that the wavefront measurement is obtained in a pupil size for which conventional subjective acuity is measured.

System 400 further includes a phoropter module 440 for determining at least a subjective spherical power (SPH_s) through a subjective refraction and for determining the best correct visual acuity (BCVA) subjectively. The phoropter module 440 can be, for example, a phoropter as described in Liang, U.S. Pat. No. 8,419,185, entitled "Methods and Devices for Refractive Correction of Eyes" which is fully incorporated by reference herein.

The phoropter module 440 may have a plurality of spherical lenses and a plurality of cylindrical lenses or may have electronically controlled lenses that can generate sphero-cylindrical corrections. The phoropter 440 is used for determining a prescription spherical power of the eye SPH through subjective refraction. The subjective refraction involves in subjective responses of the patient to a plurality of spherical powers. The phoropter module 440 is configured to dial in lenses according to an objective refraction from the objective refraction module 430 and the optical diagnosis module 450 including an objective spherical power SPH_o, a cylinder power CYL_o, an objective cylinder axis AXIS_o. The objective refraction in one embodiment is determined for obtaining the best corrected vision from wave aberration in the eye. The phoropter module 440 is also configured for allowing a patient to preview any sphero-cylindrical prescription. Viewing an acuity chart through the phoropter 440 with optical distance of 3 meters to 5 meters away from a patient, the patient is presented with a plurality of spherical settings that use the objective spherical power SPH_o as a starting point in one embodiment. From viewing the acuity chart through the phoropter, a new subjective sphere power SPH_s is found. SPH_s is obtained so that the patient obtains the best subjective acuity under CYL_o and AXIS_o at the lowest sphere power for myopic eyes. Thus, the phoropter 440 is configured to dial in the objective cylinder power (CYL_o) and the objective cylinder axis (AXIS_o) to determine a prescription spherical power (SPH_s) of the eye through a subjective refraction involving subjective responses of the patient to a plurality of spherical powers. In some embodiments, the phoropter module is configured to dial in the objective cylinder power (CYL_o) in an increment of 0.01D. The spherical power (SPH_s) may also be configured in increments finer than 0.25D, such as up to 0.06D, offering high precision in the objective measurement.

In some embodiments as shown in the embodiment of FIG. 10, the objective aberrometer module 410 and phoropter module 440 are incorporated together into one physical system, where the computer 420 provides the computing capabilities for both the objective aberrometer module 410 and the phoropter module 440. In the embodiment of FIG. 10, the display 454 is a device connected to the unitary system, where the unitary system includes objective aberrometer module 410, computer 420, objective refraction module 430, phoropter module 440, and optical diagnosis module 450.

In one embodiment, the system of an aberrometer module 410 together with a phoropter 440 is further configured with an output module 460 that is connected to computer 420, for generating a prescription and for delivering high-definition eyeglasses. The lenses of high-definition eyeglasses in one embodiment are custom manufactured using free-form technologies, which can make aberration-free lenses in addition to a lens prescription with incremental steps finer than 0.25D for SPH and CYL powers. The eyes targeted for high-definition vision in one embodiment are those ranked as "Class 1 SuperVision Optics". In such embodiments, the output module is configured to generate a prescription for high-definition or standard eyeglasses, the prescription including: a) the prescription spherical power (SPH_s) that is determined through the subjective refraction, and b) the objective cylinder power (CYL_o) and the objective cylinder axis (AXIS_o) that are determined by the objective refraction module and the optical diagnosis module. In another embodiment, the system of an aberrometer together with a phoropter is further configured for generating a prescription and for delivering standard eyeglasses with incremental steps of 0.25D. The prescription for ophthalmic lenses of the eyeglasses includes: a) a subjective spherical power (SPH_s) that is determined through the subjective refraction, b) the objective cylinder power (CYL_o), and c) the objective cylinder axis (AXIS_o) that is determined from the objective measurement of the wave aberration.

In another embodiment, the system of an aberrometer together with a phoropter is further configured with output module 460 for generating a prescription for therapeutic treatments of a conventional sphero-cylindrical correction plus high-order aberrations. The high-order aberrations to be corrected for the therapeutic treatment are determined as the excess aberrations. In one embodiment, the therapeutic treatment is achieved with eyeglasses using free-form technologies, which can correct excess aberrations in addition to a lens prescription of sphero-cylindrical correction. In such embodiments, the output module is configured to generate a prescription for therapeutic treatment of excess aberrations in addition to a conventional sphero-cylindrical correction, where the prescription includes: a) the prescription spherical power (SPH_s) that is determined through the subjective refraction, b) the objective cylinder power (CYL_o) that is determined by the objective refraction module and the optical diagnosis module, c) the objective cylinder axis (AXIS_o) that is determined from the objective measurement of the wave aberration, and, and d) the excess aberrations determined by the optical diagnosis. In another embodiment, the therapeutic treatment of high-order excess aberrations is achieved using surgical lasers.

In yet another embodiment, the system of an aberrometer together with a phoropter is further configured where the optical diagnosis module 450 identifies amblyopia and macular diseases if the tested eye reports that its best corrected acuity is worse than 20/20 through the phoropter module, such as 20/40, while optics of the eye is found to be normal or capable of seeing 20/20 or better, including eyes ranked as Class 1 SuperVision Optics or Class 2 Normal Vision Optics according to the optical diagnosis of the eye's image quality.

In yet another embodiment, the system includes a cloud computing system 425 that is in communication with the computer 420 and that is configured to perform the objective vision optimization. In some embodiments, the objective refraction module 430 and the optical diagnosis module 450 comprise numerical computation that is performed through the cloud computing 425.

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. A method of optical diagnosis of optical image quality for eye exams, the method comprising:
    obtaining an objective measurement of a total wave aberration of an eye of a patient using an objective aberrometer module, wherein the objective measurement includes a sphero-cylindrical correction and residual aberrations, wherein the sphero-cylindrical correction includes an objective spherical power (SPH_o), an objective cylinder power (CYL_o), and an objective cylinder axis (AXIS_o), wherein the residual aberrations is computed by subtracting the sphero-cylindrical correction from the total wave aberration, and wherein the sphero-cylindrical correction is obtained through objective vision optimization to achieve a best image quality for the eye;
    computing and displaying a simulated retinal image by calculating a point-spread function from the residual aberrations and convolving the calculated point-spread function with an acuity chart; and
    performing an optical diagnosis of the eye's optical image quality based on the simulated retinal image, wherein the optical diagnosis includes at least one of:
    a) determining excess aberrations in the eye, the excess aberrations being defined as a portion of the residual aberrations that are more than high-order aberrations for normal optics for seeing at least 20/20 with clear vision or for exceptional optics for seeing at least 20/12;
    b) ranking an optics of the eye into a plurality of optical grades based on the simulated retinal image;
    c) selecting the eye for which high-definition eyeglasses is delivered if the eye has exceptional optical quality for potentially achieving 20/12 acuity according to the simulated retinal image, wherein the high-definition eyeglasses are made with free-form technology with an incremental step finer than 0.25D for at least a cylinder power CYL;
    d) identifying amblyopia or macular diseases based on the simulated retinal image and a best corrected visual acuity for the eye, wherein the best corrected visual acuity is subjectively determined; or
    e) choosing an objective refraction for vision correction, the choosing comprising generating a plurality of objective sphero-cylindrical corrections that differ from each other in cylinder power, displaying and calculating a plurality of calculated retinal images that correspond to the generated objective sphero-cylindrical corrections, and reviewing the displayed plurality of calculated retinal images.

2. The method of claim 1, wherein the objective aberrometer module comprises a principle or device chosen from the group consisting of: a Hartmann-shack sensor, laser ray tracing, a spatially resolved refractometer, Talbot-Moire interferometry, skiascopic phase difference, and Tscheming principle.

3. The method of claim 1, wherein the obtaining of the objective measurement is performed for a pupil size for which conventional subjective acuity is measured.

4. The method of claim 1, wherein the objective vision optimization to achieve the best image quality for the eye comprises:
    numerically varying SPH_o, CYL_o, and AXIS_o in a plurality of combinations;
    calculating an objective retinal image quality for each combination in the plurality of combinations; and
    determining a combination of SPH_o, CYL_o, and AXIS_o to achieve the best image quality, wherein the objective retinal image quality is measured by one or more of: a Strehl ratio of a point-spread function for each combination in the plurality of combinations, a half-height width of a point-spread function for each combination in the plurality of combinations, or a modulation transfer function at a spatial frequency.

5. The method of claim 1, wherein the determining of the excess aberrations in the eye comprises a) reducing the residual aberrations in the eye by a percentage, b) computing a new simulated retinal image of the acuity chart from modified residual aberrations that equal to the residual aberrations minus the reduced residual aberrations, c) stopping the reducing of the residual aberrations in the eye when the new simulated retinal image of the acuity chart enables the eye to see at least 20/20 with clear vision or to see 20/12 with supernormal vision, and d) specifying the excess aberrations as a magnitude of the reduced residual aberrations.

6. The method of claim 5, wherein the excess aberrations are specified as some of the largest aberration terms in the reduced residual aberrations, wherein the number of the aberration terms is equal to or less than 5.

7. The method of claim 5 further comprising generating a prescription for therapeutic treatment of the determined excess aberrations in addition to the sphero-cylindrical correction, wherein the prescription includes a subjective spherical power SPH_s, the objective cylinder power CYL_o, the objective cylinder axis AXIS_o, and the determined excess aberrations, wherein the subjective spherical power SPH_s replaces the objective spherical power SPH_o and is subjectively determined using a phoropter.

8. The method of claim 1, wherein the plurality of optical grades includes: 1) "Class 1 SuperVison Optics", wherein the eye can see 20/12 or better, 2) "Class 2 Normal Vision Optics", wherein the eye can see 20/20 or better but cannot see 20/12 letters of the acuity chart.

9. The method of claim 8, wherein identifying amblyopia and macular diseases is confirmed when 1) the best corrected visual acuity of the eye is worse than 20/20, and 2) the optics of the eye is found to be normal or capable of seeing 20/20 or better, which includes eyes classified as Class 1 SuperVision Optics or Class 2 Normal Vision Optics.

10. The method of claim 8, wherein the plurality of optical grades further includes "Class 3 Aberrated Eyes", wherein the eye cannot see 20/20 letters in the acuity chart or has poor clarity even though the 20/20 letters are recognizable.

11. The method of claim 1, wherein the high-definition eyeglasses are custom manufactured using the free-form technology using a prescription that includes a subjective spherical power SPH_s, the objective cylinder power CYL_o, and the objective cylinder axis AXIS_o, wherein the subjective spherical power SPH_s replaces the objective spherical power SPH_o and is subjectively determined using a phoropter.

12. The method of claim 1 further comprising generating a prescription for eyeglasses that includes a) a subjective spherical power SPH_s that replaces the objective spherical power SPH_o and is subjectively determined using a phoropter, and b) a cylinder power and a cylinder axis that are chosen from the plurality of objective sphero-cylindrical corrections.

13. The method of claim 1, wherein the optical diagnosis is performed by an optical diagnosis module through a human-machine interface.

14. A system for optical diagnosis for eye exams, comprising:
an objective aberrometer module configured to obtain an objective measurement of a total wave aberration of an eye of a patient, wherein the objective measurement does not involve responses from the patient;
an objective refraction software module for determining, from the total wave aberration of the eye, a sphero-cylindrical correction that includes an objective spherical power (SPH_o), an objective cylinder power (CYL_o), an objective cylinder axis (AXIS_o), and wherein the sphero-cylindrical correction achieves a best image quality for the eye from the total wave aberration in the eye through objective vision optimization; and
an optical diagnosis module configured to:
a) compute a simulated retinal image under the objectively determined sphero-cylindrical correction by computing a point-spread function from residual aberrations and convolving the computed point-spread function with an acuity chart, wherein the residual aberrations is computed by subtracting the sphero-cylindrical correction from the total wave aberration;
b) display the simulated retinal image on a display device, and
c) provide an optical diagnosis through a human-machine interface, wherein the optical diagnosis includes at least one of:
c1) determining excess aberrations in the eye, the excess aberrations being defined as a portion of the residual aberrations that are more than high-order aberrations in eyes for normal optics for seeing at least 20/20 with clear vision or for exceptional optics for seeing at least 20/12;
c2) ranking an optics of the eye into a plurality of optical grades based on the simulated retinal image;
c3) selecting the eye for which high-definition eyeglasses is delivered if the eye has the potential of seeing 20/12 acuity according to the simulated retinal image, wherein the high-definition eyeglasses are made with free-form technology with an incremental step finer than 0.25D for at least a cylinder power CYL;
c4) identifying amblyopia or macular diseases based on the simulated retinal image and a best corrected visual acuity for the eye, wherein the best corrected visual acuity is subjectively determined; or
c5) choosing an objective refraction for vision correction, the choosing comprising generating a plurality of objective sphero-cylindrical corrections that differ from each other in cylinder power, calculating a plurality of calculated retinal images that correspond to the generated objective sphero-cylindrical corrections, and reviewing the calculated retinal images on the display device.

15. The system of claim 14, wherein the objective aberrometer module comprises a principle or device chosen from the group consisting of: a Hartmann-shack sensor, laser ray tracing, a spatially resolved refractometer, Talbot-Moire interferometry, skiascopic phase difference, and Tscheming principle.

16. The system of claim 14, further comprising a light source module for pupil size control during a wavefront measurement of the objective measurement, wherein the light source module for pupil size control is placed in front of the eye and is calibrated so that the wavefront measurement is obtained in a pupil size for which conventional subjective acuity is measured.

17. The system of claim 14, wherein the objective vision optimization to achieve the best image quality for the eye in the objective refraction module comprises:
numerically varying SPH_o, CYL_o, and AXIS_o in a plurality of combinations;
calculating an objective retinal image quality for each combination in the plurality of combinations; and
determining a combination of SPH_o, CYL_o, and AXIS_o to achieve the best image quality, wherein the objective retinal image quality is measured by one or more of: a Strehl ratio of a point-spread function for each combination in the plurality of combinations, a half-height width of a point-spread function for each combination in the plurality of combinations, or a modulation transfer function at a spatial frequency.

18. The system of claim 14, wherein the determining of the excess aberrations in the eye is performed through the human-machine interface with the steps of a) reducing the residual aberrations in the eye by a percentage, b) computing and displaying, by the optical diagnosis module, a new simulated retinal image of the acuity chart from modified residual aberrations that equal to the residual aberrations of step (a) minus the reduced residual aberrations, c) stopping the reducing of the residual aberrations in the eye when the new simulated retinal image of the acuity chart enables the eye to see at least 20/20 with clear vision, and d) specifying the excess aberrations as the magnitude of the reduced residual aberrations.

19. The system of claim 14, wherein the excess aberrations are specified as some of the largest aberration terms in the reduced residual aberrations, wherein the number of the aberration terms is equal to or less than 5.

20. The system of claim 14, wherein the plurality of optical grades includes: 1) "Class 1 SuperVison Optics", wherein the eye can see 20/12 or better, 2) "Class 2 Normal Vision Optics", wherein the eye can see 20/20 or better but cannot see 20/12 letters of the acuity chart.

21. The system of claim 20, wherein the plurality of optical grades further includes "Class 3 Aberrated Eyes", wherein the eye cannot see 20/20 letters in the acuity chart or has poor clarity even though the 20/20 letters are recognizable.

22. The system of claim 14, further comprising a phoropter module having i) a plurality of spherical lenses and cylindrical lenses or ii) electrically controlled lenses that can generate sphero-cylindrical corrections, wherein the phoropter module is configured to dial in the objective cylinder power (CYL_o) and the objective cylinder axis (AXIS_o) to determine a prescription spherical power (SPH_s) of the eye through a subjective refraction involving subjective responses of the patient to a plurality of spherical powers.

23. The system of claim 22 further comprising an output module configured to generate a prescription for high-definition or standard eyeglasses, the prescription including: a) the prescription spherical power (SPH_s) that is determined through the subjective refraction, and b) the objective cylinder power (CYL_o) and the objective cylinder axis (AXIS_o) that are determined by the objective refraction module and the optical diagnosis module.

24. The method of claim 22 wherein the optical diagnosis module identifies amblyopia and macular diseases if the best corrected visual acuity of the eye is worse than 20/20 through the phoropter module, while the optics of the eye is found to be normal or capable of seeing 20/20 or better, which includes eyes in Class 1 SuperVision Optics or Class 2 Normal Vision Optics according to the optical diagnosis, wherein based on the simulated retinal image, "Class 1 SuperVison Optics" is when the eye can see 20/12 or better and "Class 2 Normal Optics" is when the eye can see 20/20 or better.

25. The system of claim 22 further comprising an output module configured to generate a prescription for therapeutic treatment of the excess aberrations in addition to a conventional sphero-cylindrical correction, wherein the prescription includes: a) the prescription spherical power (SPH_s) that is determined through the subjective refraction, b) the objective cylinder power (CYL_o) that is determined by the objective refraction module and the optical diagnosis module, c) the objective cylinder axis (AXIS_o) that is determined from the objective measurement of the total wave aberration, and d) the excess aberrations determined by the optical diagnosis.

26. The system of claim 22, wherein the phoropter module is configured to dial in the objective cylinder power (CYL_o) in an increment of 0.01D.

* * * * *